United States Patent
Sinbar et al.

(10) Patent No.: US 8,186,874 B2
(45) Date of Patent: May 29, 2012

(54) THERMALLY BASED SYSTEM AND METHOD FOR DETECTING COUNTERFEIT DRUGS

(75) Inventors: Eran Sinbar, Karmiel (IL); Yoav Weinstein, Atlit (IL)

(73) Assignee: Semi-Conductor Devices—An Elbit Systems-Rafael Partnership, Haifa (IL)

( * ) Notice: Subject to any disclaimer, the term of this patent is extended or adjusted under 35 U.S.C. 154(b) by 152 days.

(21) Appl. No.: 12/672,608

(22) PCT Filed: Aug. 7, 2008

(86) PCT No.: PCT/IL2008/001090
§ 371 (c)(1),
(2), (4) Date: May 24, 2010

(87) PCT Pub. No.: WO2009/019700
PCT Pub. Date: Feb. 12, 2009

(65) Prior Publication Data
US 2011/0200067 A1    Aug. 18, 2011

(30) Foreign Application Priority Data
Aug. 8, 2007  (IL) .......................................... 185130

(51) Int. Cl.
*G01N 25/00* (2006.01)
(52) U.S. Cl. ......................................................... 374/45
(58) Field of Classification Search .................. 374/45, 374/46, 102, 103
See application file for complete search history.

(56) References Cited

U.S. PATENT DOCUMENTS

| | | | |
|---|---|---|---|
| 4,795,906 A | 1/1989 | Adams et al. | |
| 6,395,538 B1 | 5/2002 | Naughton et al. | |
| 6,771,369 B2 | 8/2004 | Rzasa et al. | |
| 6,853,447 B2 | 2/2005 | Goetz | |
| 7,126,685 B1 | 10/2006 | Paige et al. | |
| 2005/0108044 A1 | 5/2005 | Koster | |
| 2006/0289766 A1 | 12/2006 | DiMarzio et al. | |
| 2010/0230597 A1* | 9/2010 | Kumhyr et al. ............... 250/340 |

FOREIGN PATENT DOCUMENTS

| | | |
|---|---|---|
| DE | 196 29 101 A1 | 1/1998 |
| DE | 199 08 410 A1 | 5/2000 |

(Continued)

*Primary Examiner* — Lisa Caputo
*Assistant Examiner* — Jamel Williams
(74) *Attorney, Agent, or Firm* — Frommer Lawrence & Haug LLP; William S. Frommer

(57) ABSTRACT

The invention relates to a thermal system for determining the authenticity of a pharmaceutical product, said system comprises: (a) a signal generator and heat/cooling source for applying a temperature variation signal to a pharmaceutical product; (b) a thermal apparatus for: (b.1.) following or during an application of said temperature variation signal to an authentic pharmaceutical product, acquiring at predefined controlled conditions an authenticity signature of said authentic product, said authenticity signature comprises at least one temperature measurement of said authentic product, each of said temperature measurements describes the reaction over time of the authentic product to said temperature variation signal; (b.2.) storing said acquired authenticity signature in a memory; and (b.3) for a tested pharmaceutical product that corresponds to said authentic product, and whose authenticity is suspected, and following or during an application of same temperature variation signal to said tested product, acquiring at same predefined controlled conditions a test signature, said test signature also comprises at least one temperature measurement of said tested product, each of said latter temperature measurements describes the reaction over time of the tested product to said temperature variation signal; and (c) a comparison unit for comparing between said authenticity signature and said test signature.

19 Claims, 2 Drawing Sheets

FOREIGN PATENT DOCUMENTS

| | | |
|---|---|---|
| DE | 19908410 A1 * | 5/2000 |
| EP | 1 560 009 A1 | 8/2005 |
| WO | WO 96/18978 | 6/1996 |
| WO | WO 2006/090353 A1 | 8/2006 |

* cited by examiner

THERMALLY BASED SYSTEM AND METHOD FOR DETECTING COUNTERFEIT DRUGS

FIELD OF THE INVENTION

The present invention relates in general to the field of counterfeit detection systems. In particular, the present invention relates to a system and method for detecting counterfeit of pharmaceutical products. More particularly, the present invention relates to thermal based system and method for detecting counterfeit of pharmaceutical products.

BACKGROUND OF THE INVENTION

The pharmaceutical industry is a multi-billion dollar international commercial field. Like many industries however, many of the products of the pharmaceutical industry fall prey to counterfeiters who manufacture substandard or fake imitation products, and sell them for a fraction of their real market price. Worldwide, the percentage of drugs that are counterfeit has become high enough to seriously impact the revenue of major pharmaceutical companies. Even more serious is the potential health risks involved for the consumer of counterfeit drugs.

Besides the infringement of intellectual property rights as well as the breaking of other governmental laws, the Federal Drug Administration (FDA) does not yet have an all encompassing solution to the pharmaceutical industry's counterfeit problem.

There have been several attempts by the prior art to overcome the problem of counterfeit drugs, however, each of the prior art solutions has drawbacks associated with it. Some prior art technologies utilize RFID and bar coding to read the package labels to determine the authenticity of the contents contained therein. This, however, does not necessarily provide accurate results since the product itself is not directly analyzed.

The prior art has also developed drug authenticating procedures based on the concept of the spectral signature. Every drug has a unique spectral signature (or, fingerprint) determined by its molecular composition. Infrared (IR) spectroscopy is used to determine whether the molecular composition of the sample product is identical to known spectral signature of the authentic product. IR spectroscopy is the subset of spectroscopy that deals with the Infrared region of the electromagnetic spectrum. Infrared spectroscopy exploits the fact that molecules have specific frequencies at which they rotate or vibrate in relation to discrete energy levels.

U.S. Pat. No. 6,395,538 deals with the fields of bio-manufacturing and infrared spectroscopy, particularly, quality monitoring and control of a biomaterial, for instance in a biologically active pharmaceutical ingredient. Fourier transform infrared spectroscopy is used to monitor the production of a biomolecule and to fingerprint, both qualitatively and quantitatively, the biomolecule at different stages of a biomanufacturing process. U.S. Pat. No. 6,395,538, which as said relates to a spectroscopy based system, is also not concerned with counterfeit drugs on the commercial level, and therefore the system is not concerned with overcoming difficulties such as determining the authenticity of a plurality of pharmaceutical products contained within a sealed package.

U.S. Pat. No. 6,853,447 pertains to the screening and identification of materials such as pharmaceutical or food products being packaged in an automated machine. The invention utilizes an array of imaging spectrometers. The system of U.S. Pat. No. 6,853,447 performs spectroscopy in the near IR and short IR spectra. In contrast to thermography which detects the level of the IR emission from an object and the distribution of the IR emission from the object, spectroscopy checks IR reflection from the product, or more particularly, the spectral distribution of the reflection in the frequency domain. The determination of the spectra of U.S. Pat. No. 6,853,447 allows only inspection of the external surface of a product, and cannot relate to the body of the product. Therefore, when applying the spectroscopy of U.S. Pat. No. 6,853,447, each drug has to be inspected individually, outside of its container. This makes it problematic to operate when the pharmaceutical product is in a liquid state. Additionally, many capsules are coated by a thin layer of, for instance, gelatin, which blocks the near IR detector device from determining the authenticity of the drug. Moreover, utilizing such a method on a commercial scale is costly due to the amount of time required for each inspection.

U.S. Pat. No. 6,771,369 relates to the validation and identification of packaged pharmaceuticals in a retail setting. A chemical analysis and validation system preferably utilizes visual (Vis) and near infrared (NIR) spectroscopy to analyze and identify the contents of the filled prescription vial by measuring the chemical signature of the items. Other variations can also be used, for example, various forms of optical spectroscopy, UV-Vis, UV-Vis-NIR, infrared or Raman spectroscopy. The system of U.S. Pat. No. 6,771,369, similar to that of U.S. Pat. No. 6,853,447, produced by the same company, performs detection only in the near and shortwave IR spectra. As described above, operation in these spectra only allow detection of the external surface of a product, therefore, each drug must be inspected individually, outside of the container. On a commercial scale, such a limitation is a severe hindrance to the efficiency of counterfeit checking. Moreover, it is problematic to check a pharmaceutical product in the liquid state. Additionally, as described herein above, many capsules are coated by a thin layer of, for instance, gelatin, which blocks the detector device from determining the authenticity of the drug.

U.S. Pat. No. 7,126,685 describes an optical absorption spectroscopy method comprising providing a container such as a pharmaceutical bottle containing a sample, rotating the container, directing a beam comprising one or more wavelengths consisting of visible wavelengths, infrared wavelengths and ultraviolet wavelengths, and measuring characteristics of the beam after it passes through the container. U.S. Pat. No. 7,126,685 does not deal with detection of counterfeit drugs, let alone on a commercial scale, and therefore does not provide solutions to the above-mentioned counterfeit problems of the industry.

In the prior art, the development of IR technology for the detection of counterfeit drugs has been entirely limited to the field of spectroscopy, particularly near IR. Near IR spectroscopy is restricted in its detection capabilities since it is limited to surface (e.g. drug coating, outer packaging, etc.) reflection. In spectroscopy, the molecular structure of a pharmaceutical product is measured in the frequency domain, and the distinctive curvature is analyzed with corresponding signatures to determine the authenticity of the drug.

The spectroscopy based system of the prior art are relatively complicated, expansive, and large in size. Therefore, they generally cannot be produced for use by the single user, for example, in his home, for determining whether a drug is authentic or counterfeit. Furthermore, they generally cannot be made as a hand held, mobile device.

It is therefore an object of the present invention to provide method and system for determining the authenticity of a pharmaceutical product that overcome the drawbacks associated with the prior art.

It is another object of the present invention to provide a simple and low cost thermal based method and system for determining the authenticity of a pharmaceutical product.

It is an additional object of the present invention to provide method and system for determining the authenticity of a pharmaceutical product which is particularly designed for the single, end user of the drug.

It is still another object of the present invention to provide method and system that can inspect deep into a pharmaceutical product and determine counterfeit.

It is still another object of the present invention to provide method and system that can inspect and determine counterfeit of a pharmaceutical product, even from outside of the product package, and which does not require opening of the package.

It is still another object of the present invention to provide method and system that can inspect and determine counterfeit of plurality of pharmaceutical products that are packaged together, without need for opening the package.

It is still another object of the present invention to provide method and system that can inspect and determine counterfeit of pharmaceutical products from the outside of a multi-layer package.

It is still another object of the present invention to provide method and system that can inspect and determine counterfeit of a liquid pharmaceutical product from the outside of its container.

It is still another object of the present invention to provide method and system that enable a manufacturer of pharmaceutical product to design a hard to counterfeit unique signature for the product, and which can be easily verified.

Additional objects and advantages of the present invention will become apparent as the description proceeds.

SUMMARY OF THE INVENTION

The invention relates to a thermal system for determining the authenticity of a pharmaceutical product, said system comprises: (a) a signal generator and heat/cooling source for applying a temperature variation signal to a pharmaceutical product; (b) a thermal apparatus for: (b.1.) following or during an application of said temperature variation signal to an authentic pharmaceutical product, acquiring at predefined controlled conditions an authenticity signature of said authentic product, said authenticity signature comprises at least one temperature measurement of said authentic product, each of said temperature measurements describes the reaction over time of the authentic product to said temperature variation signal; (b.2.) storing said acquired authenticity signature in a memory; and (b.3) for a tested pharmaceutical product that corresponds to said authentic product, and whose authenticity is suspected, and following or during an application of same temperature variation signal to said tested product, acquiring at same predefined controlled conditions a test signature, said test signature also comprises at least one temperature measurement of said tested product, each of said latter temperature measurements describes the reaction over time of the tested product to said temperature variation signal; and (c) a comparison unit for comparing between said authenticity signature and said test signature.

Preferably, said predetermined controlled conditions comprise definition of said temperature variation signal, which in turn comprises a rate of temperature variation that is applied on the product, and a duration of time in which said temperature variation takes place.

Preferably, the corresponding temperature measurements of each of said authenticity signature and said test signature are performed at specific predefined times during or following said temperature variation signal.

Preferably, the comparison is made between a selected single temperature measurement from each of said authentic and test signatures.

Preferably, the comparison is performed between corresponding signatures of said authentic and tested products, wherein each of said signatures in turn reflects average or another mathematical operation between corresponding plurality of temperature measurements that are acquired at specific times during or following said application of temperature variation signals respectively.

Preferably, the system further comprises definition of a type of heat or cooling source for effecting said temperature variation.

Preferably, the system further comprises definition a profile of said temperature variation.

Preferably, said predefined conditions comprise definition a distance and location of the product relative to the heat/cooling source, and distance and location of the thermometer relative to the product.

In one option, said pharmaceutical product is a solid medicine. In another option, said pharmaceutical product is a liquid medicine.

In one embodiment, said authentic and corresponding test signatures comprise one or more thermal signatures of the product package.

In an embodiment of the invention said authentic and corresponding test signatures of the product are acquired while the package contains or alternatively does not contain the pharmaceutical product itself.

In an embodiment of the invention, said solid pharmaceutical product are pills that are packaged within a paper carton package. Alternatively, said solid pharmaceutical product are pills that are packaged within an aluminum or plastic package. In still another alternative, said solid pharmaceutical product are pills that are packaged within one or more aluminum or plastic packages, that are in turn contained within a paper carton package, and wherein said conditions include acquiring of the temperature measurements from outside of said paper carton package.

According to still another alternative, the liquid pharmaceutical product is contained within a container package, and wherein said conditions include acquiring of temperature measurements from outside of said container package.

According to an embodiment of the invention, the memory comprises a remote or local database, wherein the database contains plurality of authenticity signatures for one or more pharmaceutical products. Optionally, the memory comprises a remote database, wherein the comparison is performed remotely, at the location of said remote database.

According to an embodiment of the invention, the comparing unit comprises a processing unit, for performing automatic comparison between images, and wherein the authenticity is decided upon finding similarity above a predefined threshold.

Optionally, the comparing unit comprises a display for displaying one besides the other graphical indications of authentic and corresponding test signatures, for enabling visual comparison by an operator.

According to an embodiment of the invention, said temperature variation is performed by means of one or more of:

an oven; a microwave; an IR lamp; a laser beam; cooled by gas expansion; thermal electric cooler; or ultrasonic waves.

In an embodiment of the invention, said temperature variation is performed in a form of one or more of: a delta function; a step function; a rectangular function; a saw tooth function; or, a periodic function.

In an embodiment of the invention, said thermal apparatus comprises: at least one thermometer for sensing temperature of said authentic and/or pharmaceutical products; and a controller for operating said thermometer for sensing temperature at predefined times.

Optionally, one or more of the authentic pharmaceutical product and product package is intentionally engineered to introduce a distinguished authentic signature when said signature is acquired by said thermal apparatus.

Optionally, said engineering of the authentic product includes one or more coating or additive materials.

Optionally, said additive materials are air bubbles that are added at specific pattern to the product.

In still another embodiment of the invention, the authenticity verification is expanded to also include verification of meeting storage conditions of the pharmaceutical product during its life, wherein the product is coated by an additive thin film which changes its response to a temperature variation signal when exposed to destructive storage conditions, and by this changes also its authenticity signature.

In still another option, the pharmaceutical product is contained within a package, which in turn comprises internal heating element, and wherein said temperature variation signal is provided to said element in order to effect said temperature variation.

DETAILED DESCRIPTION OF PREFERRED EMBODIMENTS

Figure 1:
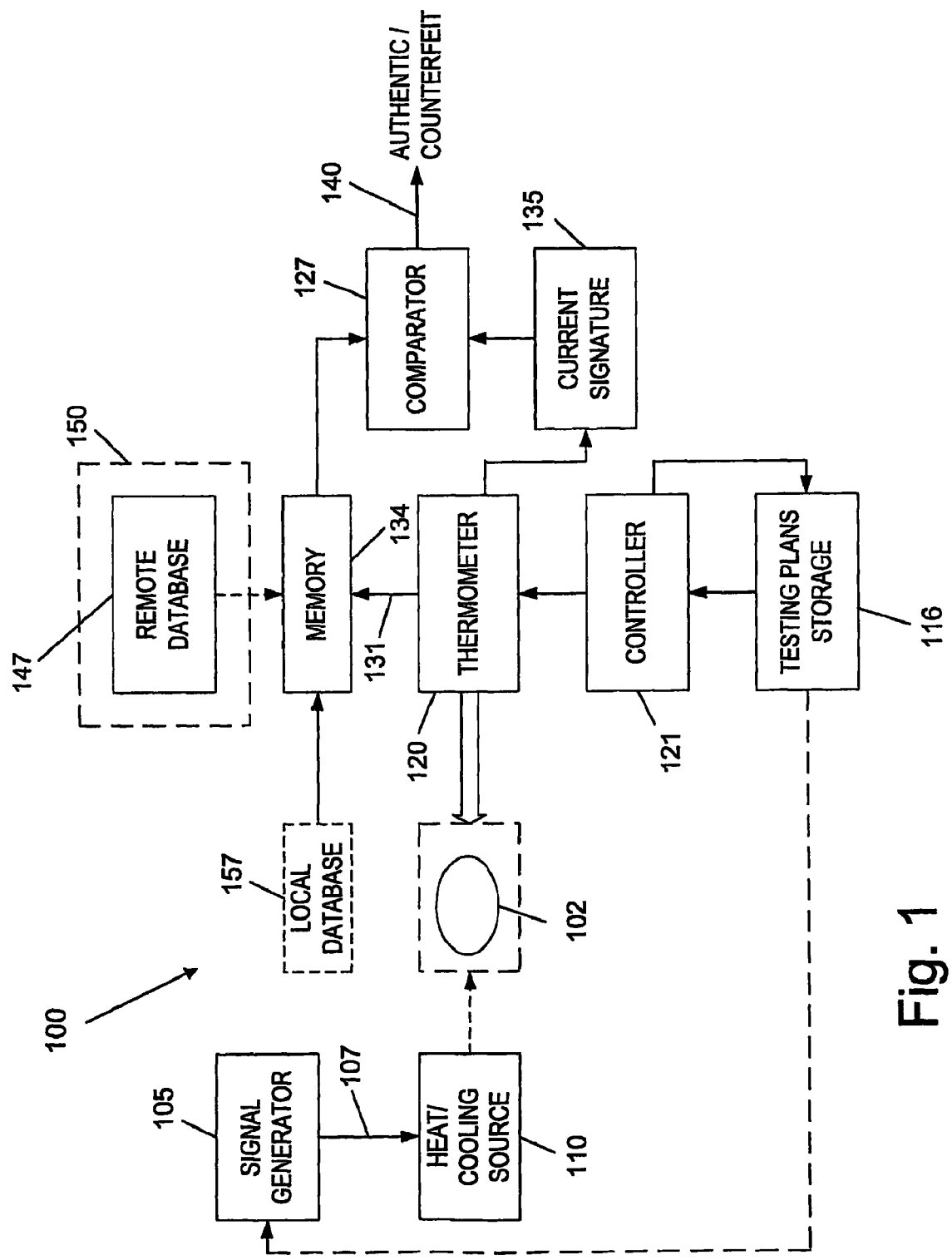
FIG. 1 illustrates a block diagram schematically showing the components of a first embodiment of the system of the present invention.

There are currently no complete solutions to the problems associated with counterfeit drugs. The present invention provides a novel, simple, and low cost thermally based system for determining the authenticity of a pharmaceutical product. The system can determine counterfeit even without removing the product from its cover, package, or container.

The term, "pharmaceutical product" as used herein refers to any form of drug, for example, a tablet, capsule or solution, and is used herein interchangeably with the term, "drug". Although the system of the present invention is particularly suitable for tablets (pills), it can still be used for determining the authentication of said other forms of drugs, such as a drug in a liquid form, or even a liquid drug contained within a container such as a bottle.

According an embodiment of the present invention, a signature of an authentic drug sample is initially collected and stored in a memory. The memory may be a database, either local or remote, which stores plurality of authentic signatures, each relating to another drug product respectively. Said initially collected signature will be referred to hereinafter also as the "authentic signature" of the drug. The thermal signature is a measurement of the temperature of the product, which is collected at a controlled, specific condition of the product. Such a specific condition may be, for example, the response of the drug product over time to a heating (or cooling) signal, the response after a specific predetermined time after the initiation of the signal, etc. The form of said heating or cooling signal is predefined, but may vary (just for example, it may be a square pulse, a saw tooth signal, etc.).

According to the present invention, the signature of a given drug product, whose authenticity is suspected, is compared to said authentic signature, for verification as to whether it is authentic or not. The comparison is made essentially in the same condition as was used upon collection of said authentic signature.

For example, the signature may be a single temperature measurement from the drug at a specific time, it may be an average of several measurements over a predefined time period, or it may involve other mathematical operations on said several measurements. Since it is assumed that a counterfeit drug product comprises a different molecular composition (and sometimes structure) than that of an authentic drug, the temperature response, e.g. as a function of time (i.e. the signature) of the authentic drug is expected to be different from that of a counterfeit drug product.

The inventors of the present invention have found that the use of a thermal system which performs temperature measurement for the detection of a counterfeit product, particularly, but not limitatively, after the providing into it a heating or cooling signal (hereinafter, for the sake of brevity both terms will be briefly referred to as a "heating signal", or "heating/cooling signal"), has considerable advantages (for example, they have a much simpler structure) over prior art detection systems of counterfeit drugs, which utilize spectroscopic devices and methods.

FIG. 1 shows in block diagram form a general structure of an embodiment of a thermal testing apparatus (100) for determining authenticity of a pharmaceutical product, according to an embodiment of the present invention. System (100) comprises a heat/cooling source (110) for heating (or cooling) a product pharmaceutical product (102) to a modified temperature. The manner of the heat/cooling change (for example, the rate of change, its duration, its type of signal, etc.) is determined by signal generator 105 and a selected testing plan. The testing plans storage 116 stores plurality of tests, and upon selection of a plan, it provides to the signal generator 105 the specific plan which is activated, which in turn determines for the signal generator 105 the type of signal to activate. Therefore, following said selection, heat/cooling source 110 applies the specific manner of heat/cooling to product 102. Controller 121 controls the operation of apparatus 100. More particularly, among others, it enables selection of a testing plan from storage 116, and according to the selected plan it determines the specific one or more times, or periods of times, for thermometer 120 to sample the temperature of product 102.

The one or more temperature samplings, separately or accumulatively, as performed by thermometer 120 form a signature for product 102. Comparator 127 compares between a signature of an authentic product and a signature of a tested product 102. The apparatus of the invention may operate in one of the following modes of operations:

a. In situ mode: The operator has in hand a first product which he knows for sure to be authentic. The user then puts the authentic product in a dedicated cell within the apparatus, and activates the apparatus. The apparatus activates a specific plan from plans 116, as selected by the user based, for example, on the type of drug, and obtains a signature of said authentic drug. This signature, which will be referred herein as "authentic product signature" is stored 131 in memory 134. As said, the signature includes one or more measurements by thermometer 120. Moreover, the signature may include results of mathematical operations that are performed on plurality of measurements. Later on, the same procedure is repeated with the second product, this time the resulted "tested product signature" is stored in tested signature storage 135. Then, comparator 127 compares between said two authentic and tested signatures, and according to some similarity threshold conditions, the comparator reaches a conclusion 140 regarding the authenticity of the product.

b. Remote signature storage mode: In this case, plurality of authentic signatures are stored within a remote data base 147, and the relevant signature is imported into the memory 134 (via the Internet, cellular communication, etc.), for comparison with a tested signature 135, which is obtained as described item (a) above.

c. Local signature storage mode: In this case, the apparatus 100 comprises a local storage (not shown) of authentic signatures. The relevant authentic signature is selected for comparison, and is stored in memory 134. The tested signature 135 is obtained as described above, and is compared by comparator 127, as before.

d. Remote comparison mode: In this case, the tested signature 135 is obtained by the apparatus as described above, and is communicated to a remote site 150. Remote site 150 has a database of authentic signatures of various drug products, and it performs a comparison within the remote site between the tested signature and the relevant authentic signature. The result of the comparison is communicated to the apparatus and displayed there. The communication with the remote site 150 may be performed via the Internet, cellular communication, etc.

Preferably, the thermometer 120 is a sensitive thermometer, either digital or analog. The sensitivity of the thermometer is important in order to sense even very minute differences between the authentic and tested signatures respectively. In another alternative, the thermometer may even not have a direct contact with the drug product (such as tablet) itself, but be up to several centimeters away from the product. Moreover, thermometer 120 may be a set of more then one thermometer that are located at different locations and distances from the product, and one or more of the thermometers may be designed from a different technology than the others.

As noted above, the apparatus of the present invention performs active thermal test of the apparatus. The apparatus initiates a specific predefined procedure, in which a specific thermal signal is applied to the product. Following said application of a thermal signal, at some predefined times or periods the temperature of the product is measured. It has been found by the inventors that there are significant differences between the response of an authentic drug product and the response of a counterfeit product. Moreover, as the form of the thermal signal can very substantially, it is possible to find a thermal signal which is most suitable to the case in question. Moreover, a comparison may include performance of several of different procedures (testing plans), and a following decision. For example, the test may include performance of 7 different test plans, it may be decided that if a drug has not passed successfully at least 5 plans, the product is counterfeit (or at least suspected).

Preferably, the drug product is in a form of a tablet. However, the apparatus of the invention may be applied for testing other form of drug products.

It should be noted the thermal change of the product temperature depends of several of the product characteristics and its surroundings: (a) it is a function of the initial product temperature; (b) it depends on the ambient temperature; (c) it depends on the product thermal conductivity; (d) it depends on the product heat capacity, (e) it depends on the product thermal convection; and (f) it depends on the product absorption of the thermal signal due to the product molecular structure. The entire surface and bulk properties of the product influence the active thermal reaction.

It should be noted that the conditions, including the heat/cooling procedure, in which the tested product signature is obtained should conform as much as possible those conditions of the corresponding authentic signature.

Heat/cooling source (110) is preferably controlled by a signal generator 105. Heat/cooling source (110), together with signal generator (105), imitate the same condition in which the authentic signature of drug 102 has been obtained. Heat/cooling source (110) may be, for instance, an oven, a microwave, an lit lamp, a laser beam, etc., for heating (or cooling, for example by means of gas expansion), an individual drug (e.g. a capsule or tablet). The signal 107 from generator 105 may be a delta function, a step function, a rectangular function, a periodic function, a saw tooth function, a combination thereof, or any other designated function. It is important to note that the response of the drug to the heat/cooling differs also depending on the type heat/cooling applied to the drug (e.g., oven, microwave, etc.), as well as on the type of temperature variation signal as provided from generator 105. Thus, whenever necessary, in order to obtain a more comprehensive characterization of the sample drug 102, more than one combination of heat/cooling source and temperature variation signal 107 may be used. Moreover, plurality of signatures that reflect the change of temperature of the drug over time may also be used. Of course, in this case, the database requires the storing of the plurality of authentic (original) signatures for a same drug for comparison, as a function of the signal form, of time, of heat/cooling source type, etc.

The apparatus of the invention is relatively simple in structure, so it may be used at the drug user's home. In view of its simplicity, it may also be provided as a hand held device.

Thus, in the above embodiment for performing the authenticity detection procedure of the present invention, active thermal procedure is performed. In this case, a drug product (such as a tablet) is heated (or cooled) by a heat/cooling source (110), which is in turn controlled by a signal generator (105). The signal generator may issue, for example, a step function, delta function, rectangle function, periodic function, etc. During at least a portion of the heating and/or the relaxation period (i.e., the cooling of the product), the temperature of the drug is measured at least once by thermometer 120, in a manner that conforms the condition as maintained when the authentic signature was collected. For example, a drug product is heated by a heat pulse until the temperature of the product is raised a predetermined amount to a modified temperature. The pharmaceutical product is then allowed to cool back to its original temperature. During at least a portion of the heating period and/or cooling period, the thermometer 120 of the present invention samples the product temperature to determine the signature of the product in question, as presently obtained, is compared, either visually on the display, or automatically, with the corresponding authentic signature of the drug as previously obtained.

As said, the signature (i.e., temperature response as a function of time, either a continuously varying response or the temperature after a specific period from the moment of initiating the heating/cooling) of the tested drug is compared to the signature of the corresponding authentic version of the drug. If the signature of the authentic version of the drug is identical, or at least highly correlated above a predefined threshold to the signature tested drug, then the tested drug is considered to be authentic. If, however, the signature of the authentic drug is not identical or highly correlated above said predefined threshold to the signature of the tested drug, then the tested product is considered to be counterfeit. If the tested drug is found to be counterfeit, necessary actions may be taken, depending on the various circumstances in which the counterfeit drug was discovered.

As previously said, in an alternative aspect the sample drug is cooled by a thermal pulse generator (e.g. a quick cooling method such as gas expansion) for a predetermined amount of time, until it reaches a predetermined modified temperature. The response is acquired during the entire pulse, during a specific time after the initiation of the pulse, even at some time after the end of the pulse. In a similar manner to as described above, also in the case of cooling, the authentic signature as well as the signature from the presently tested product, are obtained in exact same controlled conditions (i.e., same pulse, same cooling or heating temperature, same period, etc.).

In one alternative, in order to ensure accurate controlled conditions, the drug product may be put on an extended black body. Such an extended black body is known in the art, and is manufactured, for example, by CI Inc.

In another alternative, the entire testing process is performed within a temperature stabilized and controlled chamber which ensures uniform ambient temperature conditions.

It should be noted that the location of the point of contact between the thermometer and the drug product is in some cases important. Therefore, the apparatus may include a dedicated chamber for placement of the product in a specific location and orientation that will ensure contact at the desired predefined point of the product.

According to the present invention, additional secret identifying additives that affect the temperature response may be added by the manufacturer to the authentic drug during the manufacturing process in order to further distinguish it from a counterfeit drug. For instance, an internal code in a form of air bubbles may be included by the manufacturer within the drug. There are many other possible ways by which additives may be included within the drug, which affect the temperature response, but not the medical effectiveness of the drug. While such an addition to the drug has no significant effect, if any, on the medical effectiveness of the drug (and therefore, will not require additional regulatory approval by the FDA), a difference in the temperature response may be significant. Furthermore, the manufacturer of the drug may add a "code" even to the package of the drug. Such a "code" may be an additive to the package, either visible or not, which has a specific, predefined response to a temperature variation signal that can be sensed and detected by the one or more thermometers 120 of the invention. For example, such an additive material may have a specific response to a microwave, or laser heating signal, which differs from the reaction of the portions of the package.

In still another aspect of the invention, the present invention enables the determination as to whether the drug has been exposed during its life to improper heat conditions. In that case, the drug is coated by an additive (for example, edible) thin layer that changes its response to heat/cooling when exposed to a temperature above some predefined allowed limits. Just for example, the drug may be coated by a thin chocolate layer, and the authentic signature of the drug includes such layer. Later on, if the drug has been exposed to some temperature above a room temperature, this coating melts, and it affects also the signature of the drug as obtained by the apparatus of the present invention. In such a manner the apparatus of the present invention can detect not only counterfeit, but also it can ensure quality of the drug that may suffer improper storage conditions throughout its life. Moreover, in a similar manner the apparatus of the invention can also ensure the quality of a drug, and detect a drug has been mistakenly manufactured while lacking some of its ingredients. Such a lack of ingredient generally involves deviation from the authentic signature in terms of its response to a temperature variation signal. Therefore, for the sake of brevity, the quality assurance as described herein will not be distinguished throughout this application from a conventional counterfeit. In other words, the term "counterfeit" of drug relates to any deviation of the authentic drug ingredients, no matter what is the reason that has caused this deviation.

The thermal apparatus of the present invention can detect a counterfeit drug by applying one or more of the following techniques:

1. Predetermining a rate of temperature variation (i.e., minimum to maximum temperature or vice versa) that will be applied to the sample (i.e., to the "master" authentic drug, and to the drug in question);
2. The type of heat/cooling source which is used to effect said temperature change, for example, a typical oven, a microwave based oven, a laser based heating source, a refrigerator, a thermo electric cooler, etc.;
3. The profile of the temperature variation signal, i.e., a spike signal, a saw tooth signal, a step signal, a cyclic signal, etc.;
4. The distance of the product from the heat (cooling) source;
5. The option of applying averaging of the response at two or more sampling times, e.g., between two temperature measurements at times T1 and T2;
6. The location of the one or more thermostats and heat/cooling sources relative to the product.
7. As mentioned, the authenticity verification by the system of the invention includes predefined conditions that are applied to the product when obtaining the authenticity and test signatures. These conditions, although predefined, are very flexible. Therefore, if for some reason it is found that the apparatus of the invention cannot clearly distinguish between a specific authentic and counterfeit drug when one specific condition is applied, the predefined condition (including the temperature variation signal) can be easily modified in order to find a more suitable condition. The fact that the various parameters that form the possible conditions can vary within very large ranges, there is almost no doubt that a suitable condition can be found for each and any of the types of pharmaceutical products in the market, that will in turn provide a distinguishable authenticity signature for that product.

All the above options may be used, while defining the conditions for obtaining the drug signature. It should be noted that the conditions may change from one drug to another, in order to find a condition which provides a distinguishable result. Such conditions may be decided specifically for each drug upon having known counterfeit drugs, in order to find a condition that best distinguishes the authentic drug from said given drug product which is known to be counterfeit. Therefore, various conditions may be applied for various drugs or type of drugs.

It should be noted that the present invention is based on the providing of a heat (or cooling) signal to the product, and measuring the responsive temperature from the product as a function of time. Therefore, in a same manner as the drug product (such as in a form of a tablet) is authenticated, the package of the product may also be authenticated. In such a case, the temperature variation signal is provided to the package and the temperature response over time is measured. Moreover, in a same manner, the package, while including the drug product can be tested. All such manners for authenticating the drug product, with or without the package, or even the package itself, are within the scope of the present invention. It should be noted that the present invention measures the heat propagation through an object over time. Said heat propagation depends on various characteristics of the object itself, such as the object thermal conductivity, the object heat capacity, the object thermal convection, and the object rate of absorption of the thermal signal due to the product molecular structure. Therefore, for the purpose of the invention the object may be either the drug product (in any form) itself, the drug package, or the drug product while being packaged.

Example 1

A feasibility test was performed using an InSb cooled detector. The feasibility test compared between an authentic Cialis and a counterfeit Cialis, as provided by the Pharmaceutical Crime Unit, the Ministry of Health, the State of Israel.

Figure 2:
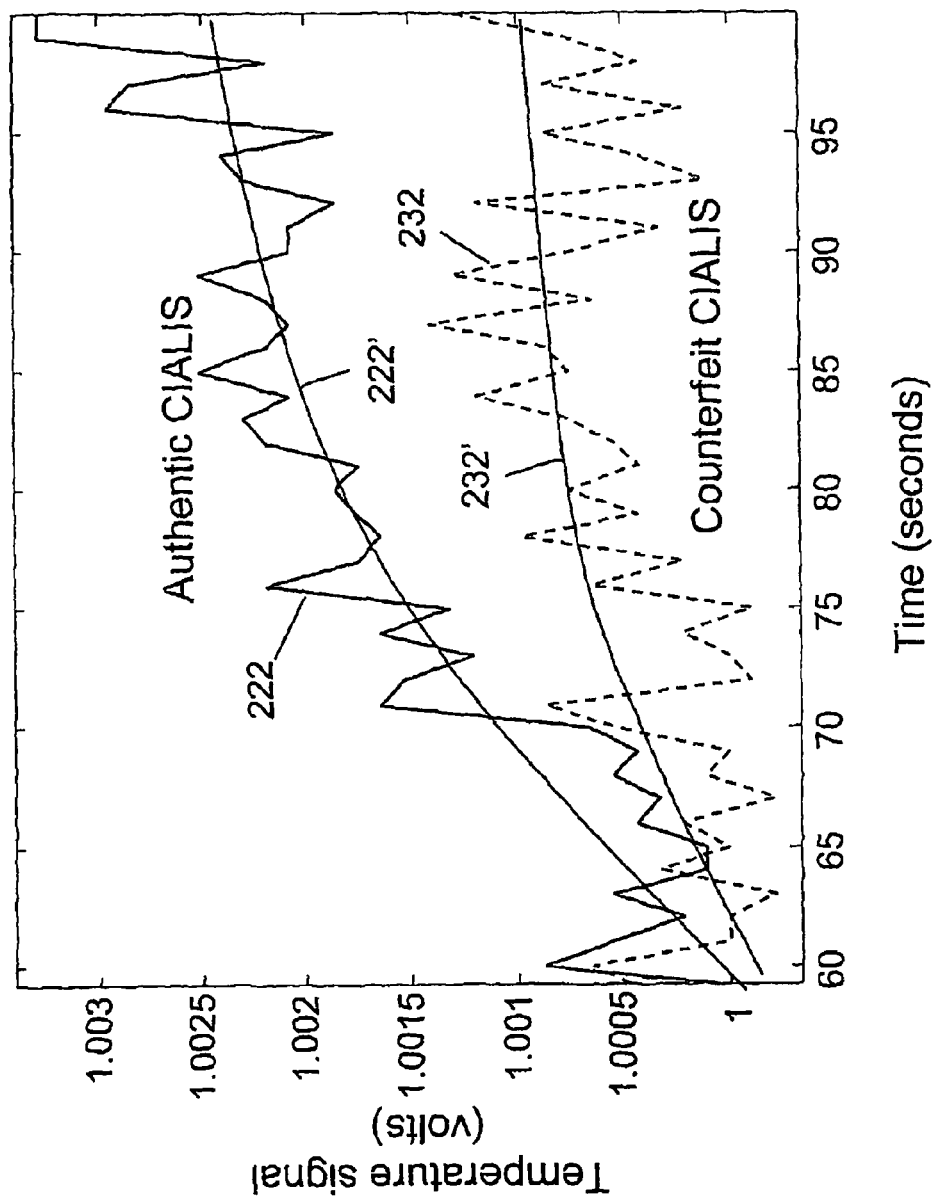
FIG. 2 illustrates results of a test which has been performed by a system according to an embodiment of the present invention.

A heat pulse was applied during 60 seconds. After 60 seconds, the heat pulse terminated, and a thermal IR detector has recorded the temperature of the drug at 1 Hz rate for a time period of 40 seconds. As can be seen from FIG. 2, the temperature signal vs. time is not the same for the authentic and counterfeit drug. More particularly, it can be seen that in this case the level of the estimated average temperature curve 222' (as sketched by the inventors for the purpose of illustration) of the authentic product measured temperature signal 222 is significantly higher than the level of the similar curve 232' relating to the tested product measured temperature signal 232.

While some embodiments of the invention have been described by way of illustration, it will be apparent that the invention can be carried into practice with many modifications, variations and adaptations, and with the use of numerous equivalents or alternative solutions that are within the scope of persons skilled in the art, without exceeding the scope of the claims.

The invention claimed is:

1. A method for determining the authenticity of a pharmaceutical product comprising:
   (a) cooling of at least the pharmaceutical product;
   (b) acquiring, over time, one or more temperature measurement of said pharmaceutical product and obtaining therefrom one or more thermal signatures of said pharmaceutical product; and
   (c) comparing said one or more temperature measurements of said product with a thermal signature of an authentic drug;
   (d) determining, based on said comparison, authenticity of said pharmaceutical product.

2. The method of claim 1, wherein said cooling comprises a temperature variation applied on the pharmaceutical product, said temperature variation comprises a rate of temperature variation.

3. The method of claim 2, wherein said temperature variation is applied in a form selected from a delta function, a step function, a rectangular function a saw tooth function, a periodic function or combination thereof.

4. The method of claim 1, wherein said cooling is performed by subjecting the pharmaceutical product to a cooling source selected from the group consisting of thermal electric cooler, black body, cooling chamber, gas expansion source and refrigerator.

5. The method of claim 1, wherein said temperature measurements are acquired at specific predefined times during or following said cooling, and wherein a change in temperature of the product as a function of time is measured.

6. The method of claim 1, wherein said temperature is acquired using a thermometer being in direct or in indirect contact with said product.

7. The method of claim 1, wherein said comparison is made between a selected single temperature measurement of said pharmaceutical product and a single temperature measurement of an authentic drug being both obtained under same predefined controlled conditions.

8. The method of claim 1, wherein said comparison is performed between an average of a plurality of thermal measurements or a result of a mathematical operation performed on a plurality of temperature measurements.

9. The method of claim 7, wherein said predefined controlled conditions comprise one or more members selected from distance of the pharmaceutical product from the cooling source; location of said pharmaceutical product relative to the cooling source; distance of the pharmaceutical product from a thermometer adapted to acquire said one or more temperature measurements; and location of the pharmaceutical product relative to said thermometer.

10. The method of claim 1, comprising comparing said one or more thermal signatures of said pharmaceutical product with one or more thermal signatures of the authentic drug obtained under same predefined controlled conditions.

11. The method of claim 1, wherein said comparison comprises determining similarities between thermal signatures of the pharmaceutical product and thermal signatures of the authentic drug, wherein a similarity above a predefined threshold is indicative of the authenticity of said pharmaceutical product.

12. A system for determining the authenticity of a pharmaceutical product comprising:
    a cooling source for cooling at least said pharmaceutical product;
    at least one thermometer for acquiring one or more temperature measurements of said pharmaceutical product;
    a comparison unit for comparing between one or more thermal signatures of the pharmaceutical product obtained from said one or more temperature measurements with a thermal signature of an authentic drug.

13. The system of claim 12, comprising a controller for operating said at least one thermometer so as to acquire said temperature measurements at one or both of predefined times and location.

14. The system of claim 12, wherein said cooling comprises temperature variations, the temperature variations comprising a rate of temperature variation.

15. The system of claim 12, wherein said controller is configured to acquire said temperature measurements at predefined times during or following said cooling.

16. The system of claim 12, wherein said comparison unit is configured to compare between one or more thermal signatures of said pharmaceutical product and one or more thermal signatures of an authentic drug being both obtained under same predefined controlled conditions.

17. The system of claim 12, wherein said comparison unit is configured to compare between one or more of a single thermal signature of said pharmaceutical product and a single thermal signature of said authentic drug; and an average of a plurality of thermal measurements or a result of a mathematical operation performed on a plurality of temperature measurements.

18. The system of claim 12, wherein said comparison unit is configured to determine similarities between thermal signatures of the pharmaceutical product and thermal signatures of the authentic drug, wherein a similarity above a predefined threshold is indicative of the authenticity of said pharmaceutical product.

19. The system of claim 18, comprising a display unit configured to display said comparison.

\* \* \* \* \*